(12) United States Patent
Brunner et al.

(10) Patent No.: US 10,251,676 B2
(45) Date of Patent: Apr. 9, 2019

(54) IMPLANTABLE DEVICE

(71) Applicant: MPS Micro Precision Systems AG, Bienne (CH)

(72) Inventors: Raphael Brunner, Biel (CH); Claude Lachat, Le Landeron (CH)

(73) Assignee: MPS Micro Precision Systems AG (CH)

( * ) Notice: Subject to any disclaimer, the term of this patent is extended or adjusted under 35 U.S.C. 154(b) by 6 days.

(21) Appl. No.: 15/123,206

(22) PCT Filed: Mar. 6, 2015

(86) PCT No.: PCT/EP2015/054719
§ 371 (c)(1),
(2) Date: Sep. 1, 2016

(87) PCT Pub. No.: WO2015/132382
PCT Pub. Date: Sep. 11, 2015

(65) Prior Publication Data
US 2017/0172624 A1   Jun. 22, 2017

(30) Foreign Application Priority Data
Mar. 6, 2014   (EP) .................................. 14158156

(51) Int. Cl.
*A61B 17/60*   (2006.01)
*A61B 17/72*   (2006.01)
(Continued)

(52) U.S. Cl.
CPC .......... *A61B 17/60* (2013.01); *A61B 17/7016* (2013.01); *A61B 17/7216* (2013.01);
(Continued)

(58) Field of Classification Search
CPC ..................... A61B 17/7016; A61B 2017/681
See application file for complete search history.

(56) References Cited

U.S. PATENT DOCUMENTS 3,976,060 A * 8/1976 Hildebrandt ....... A61B 17/8004
606/241
5,263,955 A * 11/1993 Baumgart .......... A61B 17/7216
606/62
(Continued)

FOREIGN PATENT DOCUMENTS

FR    2961386 A1    12/2011
GB    2495633 A     4/2013
(Continued)

OTHER PUBLICATIONS

International Search Report and Written Opinion of PCT/EP2015/054719, dated May 13, 2015.

*Primary Examiner* — Jan Christopher L Merene
(74) *Attorney, Agent, or Firm* — Blanke Rome LLP (57) ABSTRACT

An implantable device comprising a driving unit and a kinematic assembly joined together: the driving includes, in an hermetic capsule, electromechanical component, like an electric motor and, the battery pack, and electronic elements, while the kinematic assembly includes a reducer and an actuator, for example a lead-screw distractor, and is lubricated by body fluids. Mechanical energy is transmitted without contact from the former to the latter by a magnetic transmission.

24 Claims, 6 Drawing Sheets

(51) Int. Cl.
*A61B 17/80* (2006.01)
*A61B 17/88* (2006.01)
*A61B 17/70* (2006.01)
A61B 17/66 (2006.01)
A61B 17/00 (2006.01)
A61B 17/02 (2006.01)
A61M 5/142 (2006.01)

(52) U.S. Cl.
CPC ...... *A61B 17/7225* (2013.01); *A61B 17/8004* (2013.01); *A61B 17/8858* (2013.01); *A61B 17/663* (2013.01); *A61B 2017/00212* (2013.01); *A61B 2017/00221* (2013.01); *A61B 2017/00398* (2013.01); *A61B 2017/00411* (2013.01); *A61B 2017/00734* (2013.01); *A61B 2017/0256* (2013.01); *A61M 5/14276* (2013.01)

(56) References Cited

U.S. PATENT DOCUMENTS

| | | | | |
|---|---|---|---|---|
| 5,334,184 A | * | 8/1994 | Bimman | A61B 17/7258 606/63 |
| 5,626,581 A | | 5/1997 | Staehlin et al. | |
| 6,245,075 B1 | | 6/2001 | Betz et al. | |
| 6,416,516 B1 | | 7/2002 | Stauch et al. | |
| 7,753,915 B1 | * | 7/2010 | Eksler | A61B 17/663 606/105 |
| 8,439,915 B2 | * | 5/2013 | Harrison | A61B 17/0483 606/105 |
| 2004/0023623 A1 | | 2/2004 | Stauch et al. | |
| 2006/0047282 A1 | * | 3/2006 | Gordon | A61B 17/7016 606/86 A |
| 2006/0293683 A1 | * | 12/2006 | Stauch | A61B 17/7216 606/90 |
| 2007/0260105 A1 | * | 11/2007 | Uchiyama | A61B 1/00147 600/12 |
| 2007/0276378 A1 | | 11/2007 | Harrison et al. | |
| 2009/0076597 A1 | * | 3/2009 | Dahlgren | A61B 17/7016 623/2.1 |
| 2009/0093890 A1 | * | 4/2009 | Gelbart | A61B 17/68 623/24 |
| 2009/0112207 A1 | * | 4/2009 | Walker | A61B 17/7016 606/57 |
| 2009/0204154 A1 | * | 8/2009 | Kiester | A61B 17/7004 606/258 |
| 2009/0275984 A1 | * | 11/2009 | Kim | A61B 17/68 606/258 |
| 2012/0130428 A1 | * | 5/2012 | Hunziker | A61B 17/7016 606/258 |

FOREIGN PATENT DOCUMENTS

| | | |
|---|---|---|
| WO | WO-91/00065 A1 | 1/1991 |
| WO | WO-2010/061391 A1 | 6/2010 |

* cited by examiner

IMPLANTABLE DEVICE

RELATED APPLICATIONS

This application is a national phase of PCT/EP2015/054719, filed on Mar. 6, 2015, which claims the benefit of European Application No. 14158156.1, filed on Mar. 6, 2014. The contents of those applications are hereby incorporated by reference.

TECHNICAL FIELD

The present invention relates, in embodiments, to an implantable device comprising an autonomously supplied mechanical actuator: for example, but not exclusively, an orthopedic distractor comprising an electrical motor in a hermetic capsule and a biocompatible transmission system arranged for bidirectional displacement of bones or skeletal elements.

RELATED ART

Orthopedic distractors find application in the therapy of a plurality of diseases and malformations, in particular, but not exclusively, in the extension of long bones, but also in the surgical therapy of the spine, the jawbone, or other skeletal districts. Such techniques employ external distractor devices fixed on the bone and, more and more, internal devices that are fully implanted in the body, for example centromedullary distractor nails for the extension of long bones, jack distractors for the spine therapy, and other specialized forms of active implants.

FR2961386 describes for example a centromedullary nail that can be operated by a magnetic transmission, while US20060293683 relates to a distractor driving a lead-screw device. WO9100065 also describes a similar device.

A problem common to these devices is that of ensuring the biocompatibility of the implant containing electric motors. These devices include in fact several materials, for example control electronics, rare-earth magnets, electric windings and magnetic circuits that must not enter in contact with body tissues. The same limitations apply also to the battery used for the energy supply.

U.S. Pat. No. 6,245,075 describes a distractor with an internal or external power supply, and in which the distraction action is ensured by a hydraulic actuator. Other similar solutions are known by U.S. Pat. Nos. 5,626,581 and 6,416,516

U.S. Pat. No. 7,753,915 describes a centromedullary nail with a magnetic rotor that is driven in rotation by a rotating magnetic field generated by coils external to the body and US2004023623 describes a distractor in which the electric motor is not implanted, but external to the body, and the motion is magnetically transmitted to an internal actuator. These devices solve the problem of enclosing the potentially non-compatible components, but are not fully contained in the body, and require a relatively bulky external part that can be a nuisance for the patient.

Other forms of implantable devices comprising electromechanical actuators are also known, for example in the form of implantable pumps for drug delivery. In these devices as well as in the electromechanical distractors separation of the electric motor, electronic units and battery pack from the body tissues is of paramount importance.

WO2010/061391 discloses an automatic distractor for adjusting alveolar ridge elevation or expansion distraction gap in a patient, wherein a motor and a reduction gear are enclosed in a sealed cylinder.

SHORT SUMMARY OF THE INVENTION

It is therefore an aim of the present invention to provide a biocompatible implantable device that comprises a mechanical actuator and can operate without relying on external elements or power sources.

According to the invention, this goal is achieved by means of the object of the annexed claims, and in particular by means of an implantable device comprising a driving unit and a kinematic assembly joined together: the driving unit comprising an electric motor driving a first magnetic rotor; the kinematic assembly comprising a second magnetic rotor, magnetically coupled to said first magnetic rotor such that it can be rotationally driven by the motor, and an actuator driven by the second rotor, characterized by an hermetic capsule that encloses the driving unit, the electric motor, and the first rotor; and in that the second magnetic rotor is outside the hermetic capsule.

SHORT DESCRIPTION OF THE DRAWINGS

Examples of realization modes of the invention are indicated in the following description and illustrated by the drawings in which.

The arrangement of FIGS. 5a-b and 6a-b is also the object of the block diagram of FIG. 7.

EXAMPLES OF EMBODIMENTS OF THE INVENTION

A possible embodiment of the present invention is an intramedullary nail distractor for the correction of length deficit in long bones, like for example the femur, tibia, humerus, or any other long bone. As it is known in the art cited above, a possible therapy for such conditions comprises the surgically insertion in the medullary cavity of the target bone of a distracting nail comprising an actuator that allows to modify its overall length, and that can exert a sufficient linear force so as to promote bone growth on both sides of an artificial fracture line. Typically the implant is operated during an extended time period according to a specified elongation plan and is usually left in place, as a passive structural intramedullary nail, once the bone has reached the desired length. The relative linear speed of the connecting ends 31 and 61 are of the order of some millimeters per day.

Figure 1:
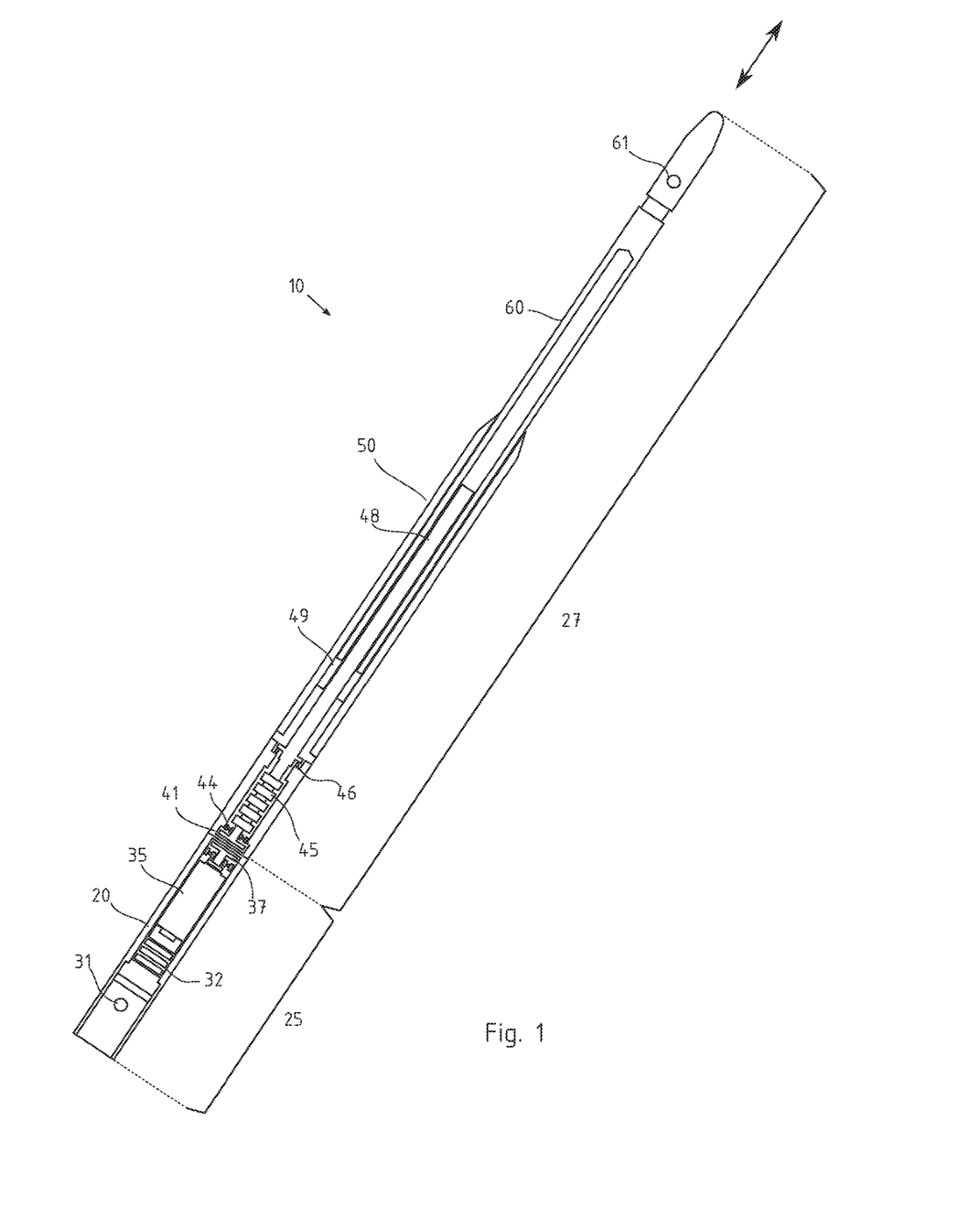
FIG. 1 represents in a simplified section view, a possible embodiment of the present invention applied to an intramedullary distractor for lengthening of long bones.
Figure 2A:
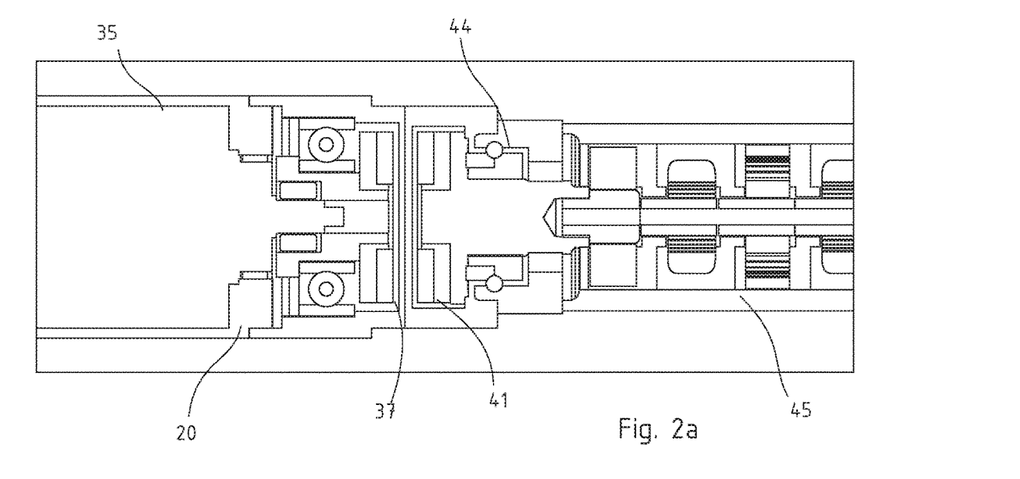
FIG. 2a shows a detail of a magnetic transmission included in an embodiment of the present invention.
Figure 2B:
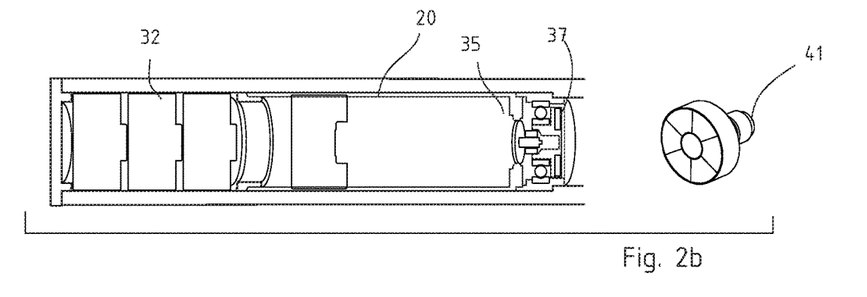
FIG. 2b shows again the magnetic transmission of an embodiment of the invention, one of the magnetic rotors having been moved away for clarity.

According to this embodiment, as illustrated by FIGS. 1 and 2a, 2b, the implantable device comprises a driving unit 25 and a kinematic assembly 27 coaxially joined together: the driving unit 25 is placed at one extremity of the intramedullary nail, and includes an electric motor 35 that can be set into rotation by a command unit, not visible in the figure, and a source of electrical energy 32, for example a stack of lithium cells or another suitable primary or secondary (rechargeable) electrical battery or supercapacitors.

The driving unit 25 is fully enclosed into a hermetic capsule 20, for example made of titanium, PEEK, or of any suitable biocompatible material. The purpose of the capsule is to prevent the ingress of body fluids into the space that encloses the electronics, the electric motor, optionally including a first reduction stage, the battery, and a magnetic rotor that is a first stage of a magnetic coupling, and effectively prevent any contact between these component and body tissue. Preferably the capsule is hermetically sealed or welded and does not present any opening so as to guarantee containment for an essentially indefinite time. More preferably, the whole driving unit is contained in a double sealed capsule so as to prevent any contamination.

In a possible variant of the invention, the battery pack may be contained in a separate hermetic capsule distinct from that encloses the motor 35, and the capsule have pass-through electric connectors to allow the transmission of electric energy from one to the other.

In some occasions, it may be advantageous to provide a separate energy source, to which the implantable device is connectable. The energy source could be positioned inside or outside the body and transmit the energy to the implantable device by means of an appropriate wired or wireless connection. This variant of the invention is particularly suitable, for example, when the actuator must be operated during a long time span, or when a suitable autonomous battery could not fit in the space available at implantation site. According to the needs, the implantable device may be entirely dependent from the external energy supply for its functioning, or include a rechargeable accumulator that can be replenished by the external energy source.

Wireless energy transmission could be obtained by electric or magnetic induction, or by an ultrasonic converter, or by any other suitable energy transmission means.

The electric motor 35 is connected, directly or indirectly, to a first magnetic rotor 37, also comprised in the capsule 20 that presents an arrangement of alternate magnetic poles. Its rotation is transmitted, by magnetic coupling, to a second magnetic rotor 41 outside the capsule 20, magnetically coupled to said first magnetic rotor such that it can be rotationally driven by the motor. FIGS. 2a and 2b represent a possible arrangement of such coupled rotors 37 and 41 as a pair of coaxial disks placed face to face. Alternative structures, for example with cylindrical rotors, are also possible.

Figure 3A:
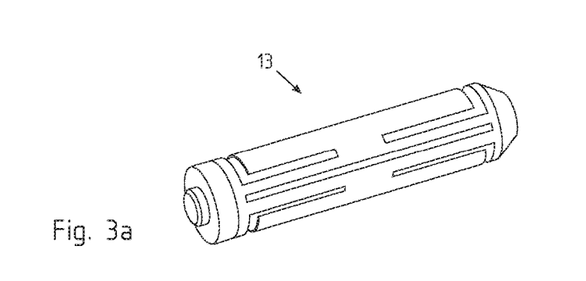
FIGS. 3a and 3b illustrate a possible embodiment of the present invention that is a spine distractor

In most orthopedic applications displacement speeds are very low, and the forces exerted are fairly high, thus requiring a reduction system. In the presented example, as shown by FIGS. 2 and 3a, the reduction is obtained by a gearbox 45, for example a cascade of planetary reductions, and by the final lead-screw 48 and nut 49 transmission that transforms the rotary motion at the output of the gear reduction 45 into a linear motion of the plunger 60 relative to the sleeve 50. A reduction stage between the electric motor 35 and the first magnetic rotor 37, inside the hermetic capsule 20 is also possible. At least part of the reduction system of this embodiment, comprising the planetary stages 45, and the lead-screw and nut assembly is not enclosed into a hermetic capsule and, therefore, it can enter in contact with body fluids, and is in fact lubricated by body fluids. Accordingly, it is integrally built with biocompatible materials like titanium, Cobalt-Chrome alloy, nitinol, BioDur® 108 alloy, stainless steel, Polyethylene, PEEK, PET, PTFE, biocompatible ceramic, or any other suitable biocompatible material. Biocompatible coatings like for example ADLC can be also applied.

In a typical application, the reduction ratio of the gearbox 45 is comprised between 500:1 and 2000:1. For example, a cascade of five 4:1 planetary stages could be used to achieve an overall reduction ratio of 1024:1. In such manner, assuming a rotation speed of the about 1000 rpm for the motor 35, the lead-screw 40 could turn at about one revolution per minute.

In other non-represented variants, the reduction system could use harmonic reducers, wobbling gears, cycloidal gears, cyclo-drive reducers, or other transmission systems achieving the desired transmission ratios.

In clinical limb-lengthening practice, the distraction plan spans over a periods of several days or weeks, during which the patient is encouraged to move and exercise the treated limb. Accordingly, the gearbox 45 and the lead-screw/nut assembly 48, 49 are arranged to resist to the axial and radial loads induced by the patient's weight and motion, plus the torque transmitted during the distraction. Preferably this is achieved by means of biocompatible axial bearings 46 in the gearbox 45. In a preferred embodiment the bearings have titanium cages and ceramic balls or rollers and are of a double-acting construction, arranged for supporting thrust both in the distraction and in the contraction directions.

FIG. 2a shows, perhaps more clearly, the disposition of the magnetic rotors 37 and 41. Each rotor comprises a plurality of magnetized zones that define a pattern of magnetic poles having alternate polarities (represented by color variations). The second rotor 41, which is not protected inside the hermetic capsule 20, has preferably the magnetic materials covered by a protective biocompatible material (not visible). Advantageously, the motor 35 in the hermetic capsule 20, the magnetic rotors 37 and 41, the reduction system 45, the lead-screw 48, and the nut 49 are all coaxially aligned and each element is directly connected to the following one, thus, the transmission is efficient and compact.

As mentioned above, the actuator of the invention is wholly contained in the implantable nail, and does not rely on external sources of energy or pressurized fluids for its operation. Another advantageous feature of the invention is that the whole transmission chain is reversible, in the sense that the linear relative motion of the attachment points 61 and 31 can be in both directions, either lengthening or shortening the implantable nail. Thanks to this feature that the distraction can be reversed, if needed.

Preferably, the driving unit also comprises a remotely-controllable command circuit that determines the rotation or the stop of the motor 35. Thanks to this feature, the motor can be operated after the implantation, based on a predetermined post-operatory plan and/or on clinical and X-ray observations. Several remote control systems can be accommodated in the frame of the invention. In a possible variant, the command circuit includes magnetic field sensors, for example hall sensors. In this manner, a surgeon can control the operation of the motor 35 by placing permanent magnet at predetermined positions outside the implanted limb, preferably in this case, the command circuit has two magnetic field sensors at spaced-apart positions, one for operating the actuator in the normal, lengthening direction, and another for reversing the distraction. In a more preferred variant, however, the remote control of the driving unit involves a wireless data link, as it will be explained in the following.

In the example shown, the lead-screw transmission is preferably self-locking, in the sense that the nail normally resists to axial loads without changing its length unless the electric motor is active. If needed, an active locking mechanism can be added to the implant. The locking is preferably assisted by short-circuiting the electric motor, and may involve any suitable form or mechanical or electric brake.

The invention admits also other forms of remote control, for example by radio transmission, near-field electromagnetic communication, ultrasounds, or any other suitable wireless communication system.

Figure 3B:
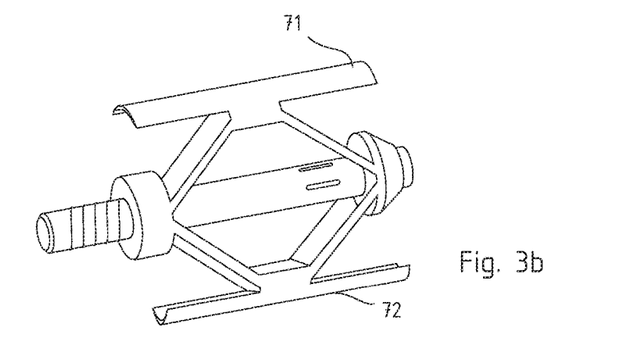
Figures 4, 5A:
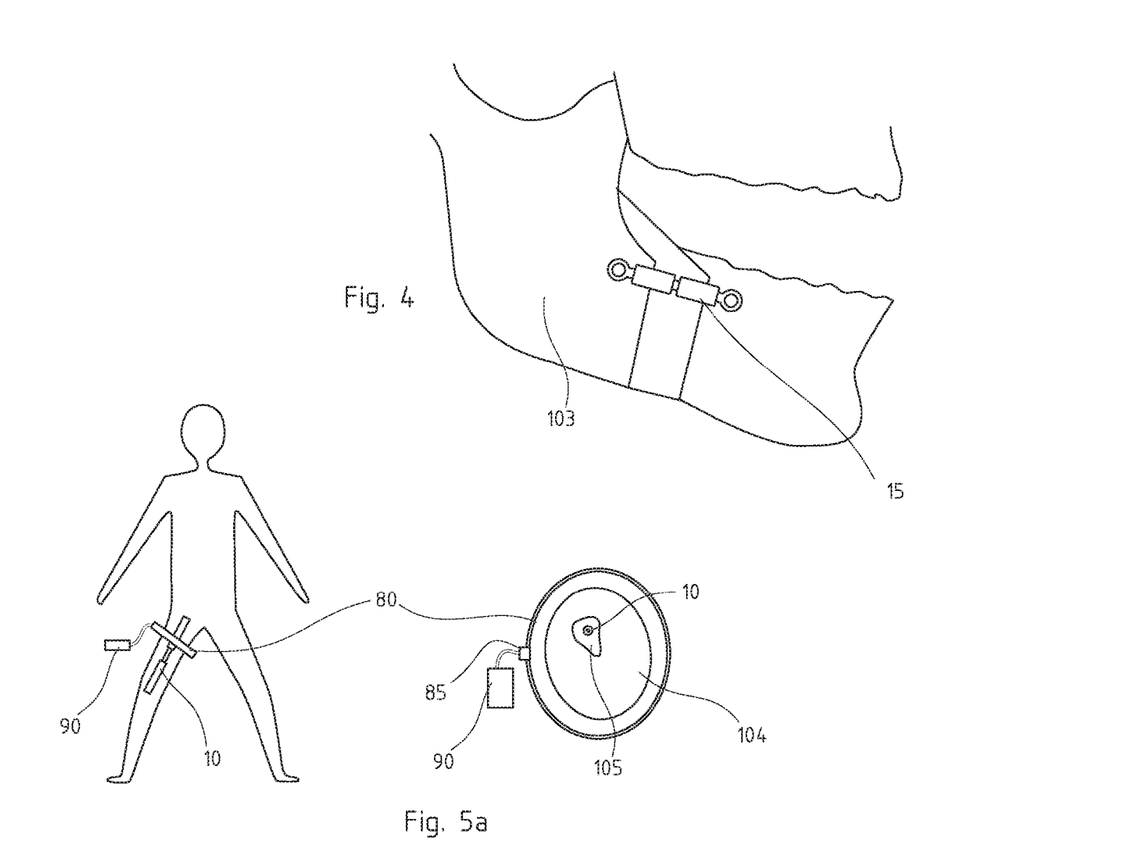
FIG. 4 shows a mandibular distractor that is an embodiment of the present invention.
FIGS. 5a and 5b show, in simplified schematic form, two possible variant of an embodiment of the invention that includes an external control unit wirelessly connected with the implantable device.

The variants of FIGS. 1, 2, 3a, 3b are specially adapted for an implantation in the medullary canal of long bones. This is not, however, the only application of the invention. FIGS. 3a, 3b illustrate a variant of the invention applicable to other parts of the skeleton, in particular in the treatment of the spine and of scoliosis. In this variant the lead-screw 48 operates an articulated jack 13 that can be used as implantable spine distractor. FIG. 4, on the other hand, illustrates the possible implantation of a device 15 according to the invention used as a Cranio-Maxillo distractor. In this application, the implant is fixed outside of a bone, in this case a mandible.

Other applications of the inventive implant are possible, including limb length correction, both congenital and post-traumatic; poliomyelitis; pseudoarthrosis; bone stump extension after amputations; bone transport after tumor resection; unilateral or bilateral impaired or abnormal growth; partial or total hip replacement, tumor prosthetic knee; cosmetic lengthening; Orthognatic surgery; correction of jaw deformities; Craniomaxillofacial distraction; Alveolar Ridge distraction; Multi-vector distraction; and, in the spine district, non-fusion scoliosis and other orthopedic conditions.

The invention is not limited to orthopedic application either, other not represented embodiments may include instead of the lead-screw and nut, different actuators like for example an impeller, positive displacement pump, or any other device requiring a movement or a displacement.

According to an embodiment, the present invention comprises, in the implantable device, a rechargeable energy storage 32 that could comprise for example one or several lithium-ion cells, or other electrochemical cells, or a high-value capacitor, like for example a double-layer capacitor, a supercapacitor, a pseudocapacitor, or any suitable energy storage device. The energy necessary to the functioning of the implantable device is received wirelessly by means of suitable antennas from an external control unit 90 and accumulated in the storage means 32.

Figure 7:
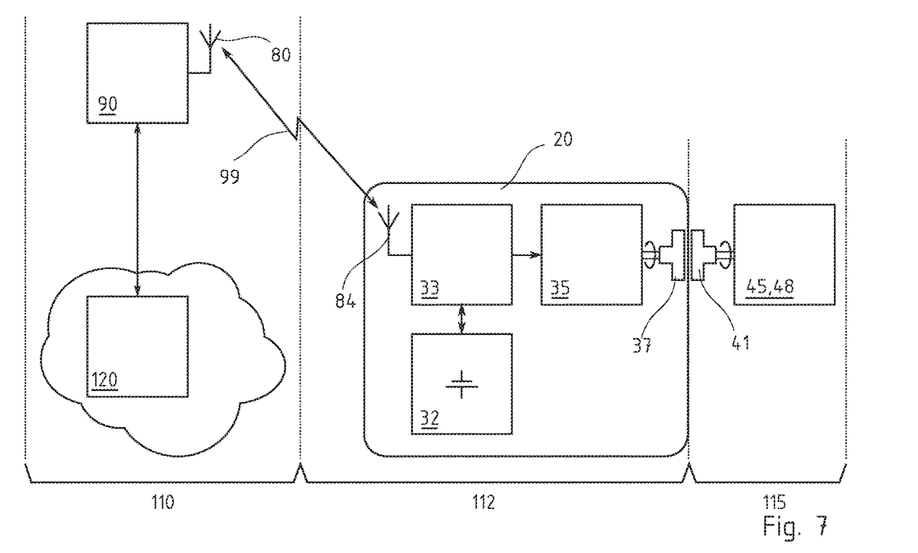

FIG. 7 illustrates in block fashion the structure of this embodiment of the invention. The hermetic capsule 20 includes, in addition to the magnetic rotor, a receiving antenna 84 connected to a control electronic unit 33. The antenna 84 picks up an AC or RF signal generated by a transmitting antenna 80 and an external module 90, which is then rectified by the electronic circuit 33 and stored in the storage means 32. The electronic circuit 33 comprises also a motor drive subunit that is arranged for driving the motor 35 according to a determined distraction plan, for example. Advantageously, the electronic circuit 33 is arranged for charging the storage means 32 when the antenna 84 picks up a sufficient AC or RF signal, and can operate autonomously using the electric energy accumulated in the storage means when the external excitation antenna 80 is inactive or detached from the patient. In this manner, the patient in whom the device of the invention is implanted needs not be constantly in connection with the external device. In some cases, however, for example in the distraction therapy of the femoral bone, the energy required may exceed the capacity of the storage 32, and the patient will need to wear the external device during treatment. The implantable device may continue to function between distraction cycles for diagnostic purposes, however.

Importantly, the electronic unit 33, the energy storage 32, the motor 35, and the magnetic rotor 37 that is driven by the motor, are enclosed in a hermetic volume defined by the capsule 20, thereby avoiding any risk of contamination or lack of biocompatibility. At the same time, the implantable device can be operated for an indefinite time by providing an adequate number and duration of recharges via the wireless link 99. As it has already been mentioned, the hermetic capsule 20 may include also other elements, like for example a reducing unit between the motor 35 and the magnetic rotor 37, or additional electronic elements like a wireless radio interface, sensors for acquiring force, temperature, or other useful variables, processing units, memory means, and so on.

Tests have shown that a suitable level of electric power can be transmitted through the wireless link 99 also when the receiving antennas is enclosed into an integral metallic capsule 20, by judiciously choosing the excitation frequency and/or the capsule material. If an especially low level of loss is sought, the capsule 22 could be realized in a suitable dielectric biocompatible material, for example PEEK, bio-ceramic, or bioglass. A metallic capsule is however preferable, both for its superior strength, and because it shields the inner electronic elements from unwanted electronic interference.

The best results have been obtained so far with low-frequency magnetic excitation for example comprised between 10 kHz and 100 kHz. In this region of the electromagnetic spectrum, the receiver and transmitter antennas can effectively be realized by suitably dimensioned coils. Other form of antennas and other values of frequency are however also possible.

Advantageously, the wireless link 99 can be used not only to charge the energy storage 32, but also for exchanging information in digital form between the external control unit 90 and the electronic module 33. Preferably the transmission is bidirectional: the downlink (from the controller unit 90 to the implanted device) can be used for example to download the distraction plan, which the physician can modify or adapt along the treatment based on the clinical at its disposal. The uplink in the reverse direction can be used to transfer several information including clinical parameters and/or diagnostic information relative to the actuator itself. Such information may comprise, for example, the linear position of the lead-screw i.e. the amount of distraction so far attained in real time, the force acting on the implant, the body temperature, the temperature of the actuators, the state of the storage unit, and so on. Usefully, the electronic unit 33 may be arranged to transmit to the controller 90 the intensity of the variable RF or AC field, and this information can be in real time used to position the excitation antenna 80 and optimize its coupling with the receiver 84.

In a preferred variant, the control unit 90 includes a rechargeable battery and can operate without a permanent connection to the mains electric network.

The inventive system represented in FIG. 7 may thus be subdivided in three distinct zones:

The external zone 110 includes the control unit 90, the transmitting coil 80, and possibly other devices 120 communicating with the control unit 90, for example a remote computer or a remote mobile device establishing an internet connection with the control unit 90. The devices in this zone are not implanted and have no or limited contact with the human body.

The protected zone 112 includes all the elements of the implant enclosed by the hermetic capsule 20. The capsule 20 is so constructed that these elements cannot under any circumstance come into contact with the living tissues. Preferably the hermetic capsule has a continuous impervious boundary that is not interrupted by feedthrough connectors, passages or openings of any kind. Elements in the protected zone can interact with the external zone 110 by electromagnetic interaction via the antenna 84, and with elements in the 'wet' zone 115 by the magnetically coupled rotors 37, 41.

Finally the 'wet' zone 115 encompasses at least the second magnetic rotor 41, the reducer 45, and the actuator, which can be for example a lead-screw 48 or another suitable mechanical device. These elements may be designed to operate in continuous contact with body fluids and live tissues.

Figure 5B:
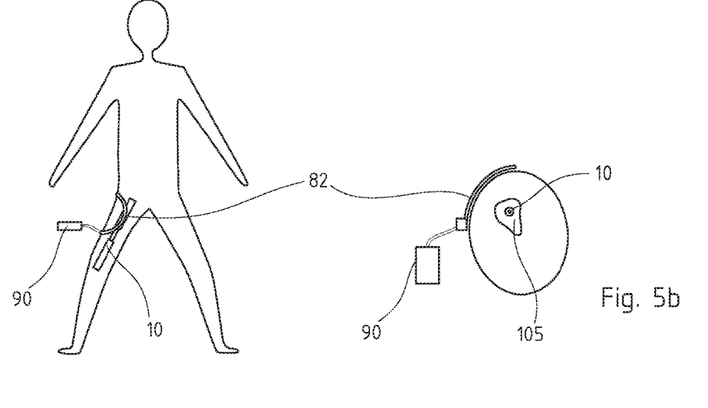

FIGS. 5a and 5b illustrate two possible setups that may be used to wirelessly couple the external control unit 90 with the implantable device. In FIG. 5a one excitation coil 80 encircles a limb in which the device is implanted (here a thigh 104, the implant 10 being in the femoral bone 105) A suitable connector 85 joins the coil 80 with the external control device 90.

Even if the figure does not show it, it must be understood that the external antenna is not limited to one coil and could in fact comprise any number of them. One could for example conceive to use two equal parallel coils in a Helmholtz configuration for increasing the intensity and the uniformity of the magnetic at the implantation site. In many cases, however, one single coil is sufficient, and, the placement of the transmitter coil 80 is not critical. This arrangement generates a magnetic field that is prevalently axial relative to the treated limb. The receiver coils within the implant, not shown in the figures, will preferably be wound around the same axis, in order to maximize the coupling.

FIG. 5b illustrates an alternative arrangement in which the transmitter coil does not encircles the limb, but is essentially parallel to the thigh's skin. Preferably, as in the drawing, the transmitter coil 82 is bent, or even flexible, to conform to the limb's shape. In this case, the magnetic field is prevalently transverse relative to the treated limb, and the receiver coil or coils are wound in accordance to this. Since the coil needs not be worn around the limb, this solution is more comfortable.

As above, also this variant the invention is not limited to a single transmitter coil, and another coil could be placed symmetrically, to enhance the magnetic field at the implant. The invention encompasses arrangement with any number of excitation coils in whichever configuration.

Figures 6A, 6B:
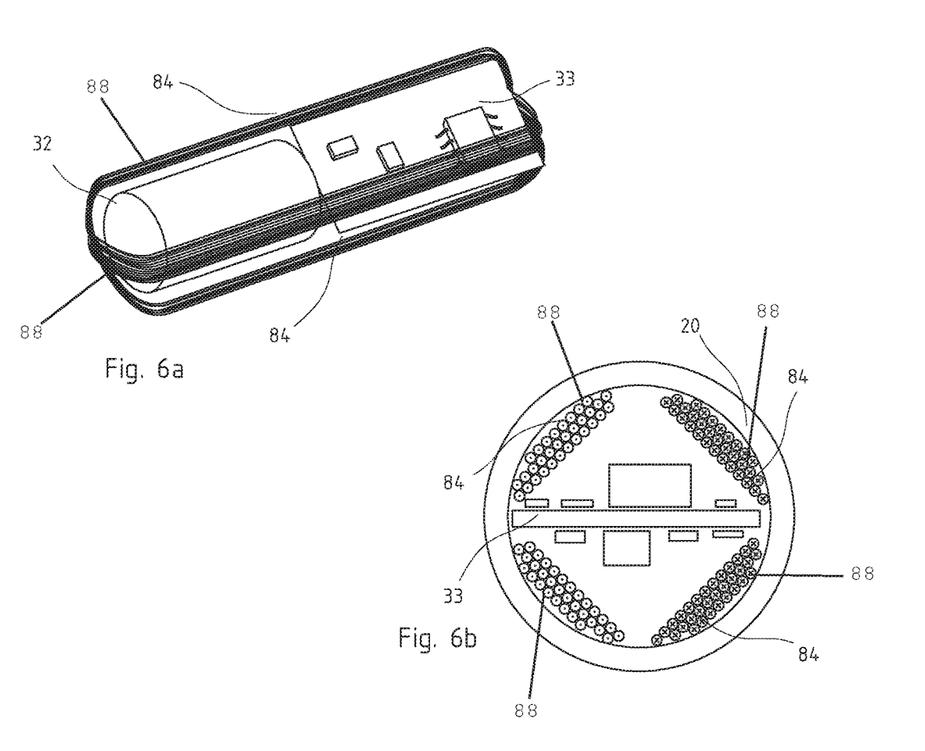
FIGS. 6a and 6b show schematically a possible structure of an implanted electronic module with receiving antennas and an energy storage suitable for use with the embodiments of FIGS. 5a and 5b.

FIGS. 6a and 6b represent a possible disposition of some of the subunits contained in the hermetic capsule 20. The electronic circuit 33 realized on a printed circuit board is connected to a supercapacitor 32, and two receiving coils 88 are wound at 90° from one another in order to couple with a variable magnetic field predominantly in the transverse direction. This arrangement is suitable for use with the bent coil excitation of FIG. 5a. Thanks to the double crossed receiving coils, the coupling is essentially omnidirectional from all transverse directions, thus the transmitting coil 82 can be placed freely in this plane. It must be understood, however that the invention could also present a single coil, or a higher number of coils, in the hermetic capsule 20.

In a possible variant (not represented) the receiver unit is arranged to determine its orientation relative to the magnetic field, for example thanks to a plurality of differential receiving coils with different orientations and positions, This information can be used in real time to align the external excitation coil with the implant.

The motor, the magnetic rotor and other components that may be present in the capsule are not shown in the FIGS. 6a, 6b for simplicity's sake.

Should the axial disposition of FIG. 5a be preferred, the arrangement of the receiving coil 88 would preferably be adapted in order to optimize the coupling with an axial magnetic component rather than a transverse one. The receiving coil could for example be an axial solenoid wound around the circuit 33 and the supercapacitor 32.

Preferably, the control unit 90 and/or the receiving unit 33 may be arranged to tune in real time the frequency of the excitation field, as well as the electric inductivity and/or capacity of the transmitter and receiver antennas, or of tank circuits attached thereto, in order to establish and maintain a resonance condition between them, thus enhancing the energy transfer between the external antennas 80, 82 and the receiving ones 84. The transmitter coil may be excited with high current intensities (typically between 1 and 50 A) in order to attain the desired power transfer.

Since the wireless connection 99 enables data upload from the implanted device to the external controller, this channel can be used to feedback information that are used to achieve and maintain resonance in a control loop. Optionally, the control unit 90 is arranged for controlling the power transfer level in order to keep the temperature of the implanted device within predetermined limits.

As the device is required to generate high forces (of the order of 1 kN or higher), it might be necessary to drive the electric motor with high power and current. The instantaneous power required by the motor might then be higher than the maximum power that can be transmitted wirelessly by the link 99 and, in this case, the charge time could be longer than the operate time. The implantable device could therefore be operated in a cyclic manner, with intermitted distraction period interleaved with longer charging periods. The use of supercapacitors for the energy storage 32 is especially advantageous in this kind of applications, owing to the high power density of these components.

Communication between the external control unit 99 and the implanted processor 33 can be obtained by any suitable modulation of the magnetic field generated by the antenna 80. Changes in the power consumed in the receiver circuit are visible on the transmitter side through the backscatter effect. It would also be possible, however, to create a radio wireless link between the controller 80 and the implanted processor on an independent frequency, and using separate antennas.

The magnetic field generated by the antenna 80 could be modulated by a FSK (Frequency-Shift Keying) scheme. Advantageously, FSK is relatively insensitive to amplitude changes that may be induced, for example, by patient's motion, and has no impact on the power transfer. This modulation scheme, however, interferes with the resonance condition. To maintain resonance one should either limit the modulation depth to less than the width of the resonance peak, with a consequent degradation of the link budget, or increase the bandwidth of the tuning controller so that it can follow the modulation shifts.

ASK (Amplitude-Shift Keying) is another possible modulation that could be used both in the downlink channel and in the uplink (backscatter) one. It is relatively simple to implement, but it presents some drawbacks:

ASK is sensitive to all sort of changes in the propagation conditions and, in particular, to any movement or orientation change of the transmitter coil or of the implant relative to one another. This means that the decoder should be equipped to discriminate these extraneous variations from the modulation.

In all forms of ASK (especially in On-Off Keying), the duty-cycle of the carrier is significantly lower than 100% and, consequently, the power that can be transmitted on the wireless channel is considerably reduced.

According to a variant of the invention, the information transmitted from the external unit 90 to the implanted device is encoded according to a double-modulation principle in which different symbols are encoded as predetermined sequences of frequency and/or amplitude shifts. In a preferred embodiment, represented by FIG. 8, the magnetic field is modulated to represent two values, denoted '0' and '1', which are encoded by different temporal rates of amplitude changes. In the represented example '0' is encoded by a square amplitude modulation at frequency $f_M=f_c/8$, where $f_M$ and $f_c$ denote, respectively, modulation and carrier frequencies, while '1' is encoded by a square amplitude modulation at frequency $f_M=f_c/10$. Other factors are however possible.

Figure 8:
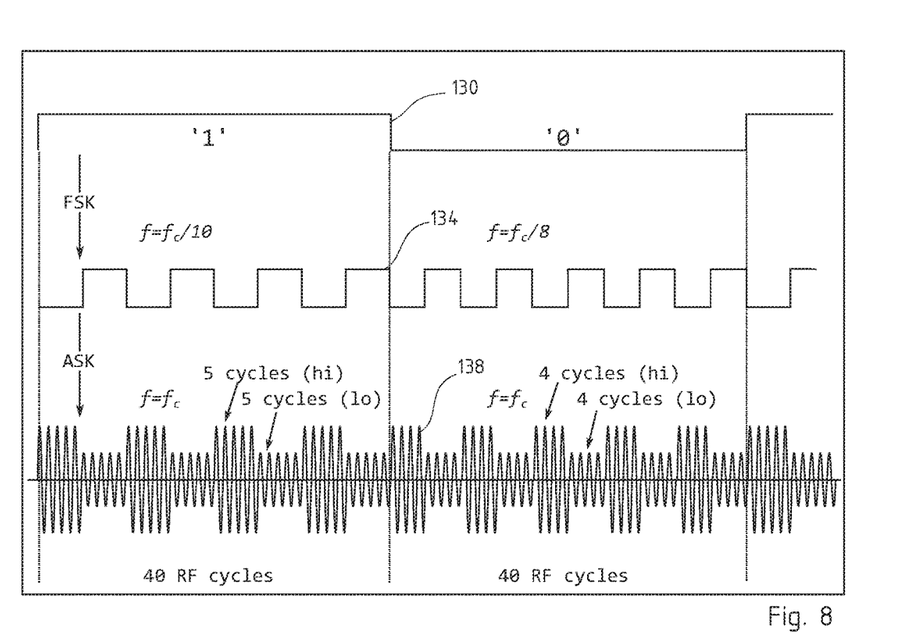
FIGS. 8 and 9 illustrates a possible modulation scheme for the wireless link of the previous embodiments.

The modulation could be phase-synchronous with the carrier, as in the example, and the symbol duration is preferably constant. In the example, each symbol (or bit in this case) is encoded by an interval of 40 RF cycles, that is the least common multiple of 8 and 10, but other factors can also be used.

Asynchronous modulation is also possible and can be advantageous in certain conditions. In particular, due to limitation of space and energy, the control unit 33 could be equipped with a limited-power microcontroller that operates on an internal clock whose frequency may not be very exact. At the same time the carrier's frequency may be shifted in order to achieve a resonance condition at the transmitting antenna 80. In this case, an asynchronous signal available at the receiving antenna could be processed by a demodulator stage and either an hardware UART interface a suitable piece of software of the microcontroller. If the modulation is asynchronous, it is preferable that the carrier frequency be sufficient high in comparison to the data speed, which is the case in the present application.

Expressed in another way, the modulation scheme of FIG. 8 can be regarded as a double modulation in which the original message 130, consisting in an arbitrary bit sequence, is first modulated by FSK, obtaining a variable-frequency digital signal 134 which is then modulated by ASK and gives the double-modulated signal 138. This double modulation could also be used in real implementation of the modulator of the device of the invention. The signal 138 could however also be directly synthesized, or obtained by any suitable algorithm.

Advantageously in this mode of modulation the frequency of the amplitude changes, which could be indicated as 'chip rate' is fairly high. Assuming a carrier frequency of 20-30 kHz, which is typical, the chip rate would be of 2-3 kHz or higher, well above the region of spectrum of body movements. As a consequence, the amplitude variations caused by motion can be filtered out fairly easily in the receiver thus recovering the frequency-variable message 134 that delivers the original message 130 by FSK-demodulation. As above, other demodulation schemes can be adopted by concrete implementations.

Another advantage of the double-modulation scheme described above is that the resultant signal has essentially constant frequency $f=f_c$. The modulation has negligible impact on the frequency of the modulated signal and resonant wireless charging is possible.

Further, the double modulation scheme proposed has the advantage that the average AC current of signal 138 is constant. The power transferred does not depend on the modulation state.

Figure 9:
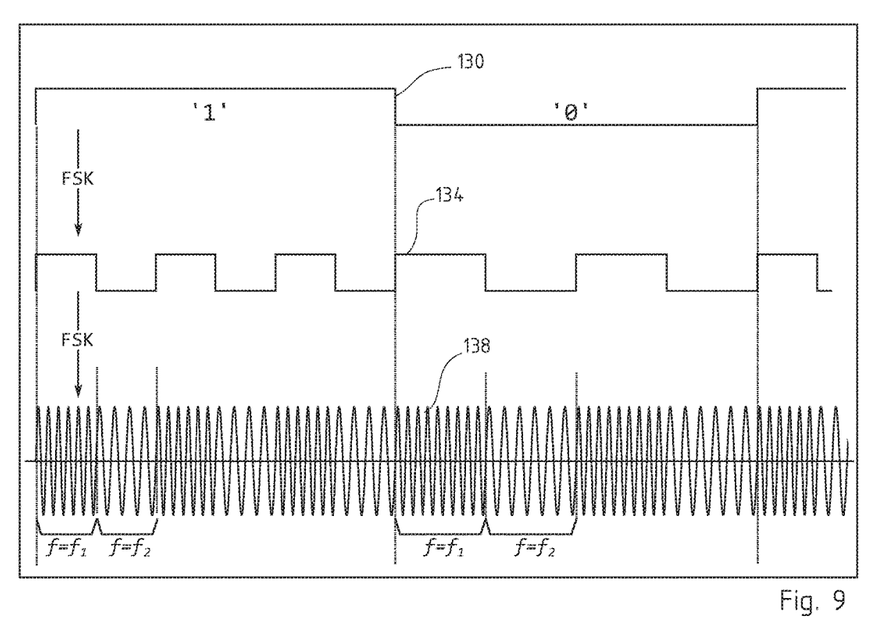

According to another possible modulation scheme, illustrated in FIG. 9, the present invention employs a double FSK modulation scheme, wherein the message 130, consisting in a bit sequence, is first modulated by FSK obtaining a variable-frequency digital signal 134 which is in turn used to generate the double-modulated AF signal 138. The double-modulated signal 138 consists in a series of intervals containing a pure tone having either of two possible frequencies: $f=f_1$ and $f=f_2$. Values '1' and '0' are encoded by the different rates of frequency change in the double-modulated 138, in contrast with the variant of f FIG. 8, which used different rates of amplitude changes to encode the '1', '0' values.

As in the previous case, the two stages of modulation of FIG. 9 are presented here simply by way of example, and the double-modulated signal 138 could be synthesized directly from the message 130 without generating the intermediate signal 134. As seen previously, the modulation can be synchronous or asynchronous with the carrier phase, with the second solution being preferable when the implanted controller 33 is equipped with a simple microcontroller.

This modulation system presents, as the previous one, the advantage of a high immunity from motion-induced amplitude fluctuations. Moreover, since the amplitude is constant, the transferred power can be higher.

While the system of FIG. 8 operated at essential constant frequency, the frequency in this variant is variable. Preferably the external control unit 90 includes a tuning system, arranged to tune automatically the resonance frequency of the emitter antenna 80, or of a tank circuit connected thereto, in order to follow the frequency variations of the modulated signal 138.

Tests and simulations have shown that it is possible to design a tunable tank circuit for the antenna 80 that can be controlled sufficiently fast to achieve an adequate data transfer speed for the present application, while maintaining the resonance condition, and a maximal power transfer.

The uplink channel of communication from the implanted controller 33 to the external unit 90 is preferably realized, as already mentioned, utilizing the backscatter effect: the implanted microcontroller 33 modulates the load seen by the receiving antenna 84, and these variations are sensed as voltage or current signals at the transmitter antenna 80. The advantage of this manner of communicating is that the implanted controller needs not include a high-frequency generator, but simply has to controls a variable load, which, in a simple realization, could reduce to a transistor connected across the terminals of the coil 84. Other dispositions are also possible, however.

Preferably, the uplink channel adopts also a modulation scheme, or better a double modulation scheme, in order to avoid movement-induced errors. In a preferred variant, which is not however the only one possible within the scope of the invention, the load on the antenna 84 is switched at either of two possible frequencies: $f=f_1$ and $f=f_2$. Values '1' and '0' are encoded by the different rates of frequency change. As per the downlink case, this modulation could be generated by a standard microcontroller.

The invention thus proposes a use of an AC magnetic field to transfer data or data and energy from an external unit to a device implanted in a human or animal body, wherein the AC magnetic field is double-modulated in frequency and/or amplitude by a digital signal having variable rate, the rate of change of the digital signal representing symbols or bits of information. Even if this modulation scheme has been presented in connection with a distractor device, it could be usefully adopted for any kind of implanted device, including those that do not include a mechanical actuator.

REFERENCE NUMBERS 10 intramedullary distractor
13 spine distractor
15 Cranio-Maxillo distractor
20 hermetic capsule
25 driving unit
27 kinematic assembly
31 attachment region
32 energy source or rechargeable energy storage
33 implanted control unit, microcontroller
35 motor
37 magnetic rotor
40 lead-screw
41 magnetic rotor
44 radial bearing
45 planetary reductions
46 axial bearing
48 actuator, lead-screw
49 nut
50 sleeve
60 plunger
61 attachment region
71 flat pusher
72 flat pusher
80 charging coil (axial)
82 charging coil (bent)
84 receiver antenna
85 connector
90 control unit
103 maxilla
104 leg
105 femoral bone
110 External zone
112 Protected zone
115 'Wet' zone
120 network-connected device
130 message
134 FSK modulated signal
138 double-modulated signal

The invention claimed is:

1. Implantable device comprising: a driving unit and a kinematic assembly coaxially joined together: the driving unit comprising an electric motor driving a first magnetic rotor; the kinematic assembly comprising a second magnetic rotor, magnetically coupled to said first magnetic rotor such that it can be rotationally driven by the motor, and an actuator driven by the second rotor, further comprising an hermetic capsule that encloses the driving unit, the electric motor, and the first rotor; and in that the second magnetic rotor is outside the hermetic capsule, wherein the actuator comprises a lead-screw coaxially aligned with the driving unit and the kinematic assembly.

2. The implantable device of claim 1, wherein said actuator consists a leadscrew-nut distractor or a jack distractor.

3. The implantable device claim 1 having a first connection region and a second connection region for attaching to bone, the actuator being arranged as to generate a relative motion of said first and second connection regions.

4. The implantable device of claim 1, wherein said second magnetic rotor drives said actuator through a reduction unit.

5. The implantable device of claim 1, wherein said actuator is able to be lubricated by body fluids.

6. The implantable device of claim 1, further comprising a storage of electrical energy in the hermetic capsule.

7. The implantable device of claim 4, in which said reduction unit comprises one or more bearing systems capable of transmitting axial loads.

8. The implantable device of claim 1, in which said hermetic capsule consists in a hermetic titanium tube or other biocompatible material.

9. The implantable device of claim 1, wherein the device further includes a control unit arranged for starting and/or stopping and/or reversing the motion of the electric motor.

10. The implantable device of claim 1, wherein the device further includes a control unit is-arranged for wirelessly exchanging data and/or energy with an external device.

11. The implantable device of claim 1, wherein the device further includes a control unit is-arranged to convert an AC signal picked up by the one or several receiving coils and charge an energy storage means comprised in the hermetic capsule.

12. The implantable device of claim 10, wherein a coupling between the implantable device and the external device is essentially omnidirectional.

13. The implantable device of claim 1, wherein the device further includes a control unit is-arranged for demodulating a signal transmitted by said external device, the signal comprising a message that is encoded as temporal rates of change of frequency and/or amplitude.

14. A system comprising an implantable device according to claim 13 and an external control device, said external control device comprising a transmitting coil arranged to generate and maintain a resonant magnetic field for charging an energy storage means comprised in the hermetic capsule.

15. The system of claim 14, wherein the external control device is arranged for transmitting a signal to said control unit, the signal comprising a message that is encoded as temporal rates of change frequency and/or of amplitude.

16. The system of claim 15, wherein the implantable device further comprises a control means arranged to tune automatically the resonance frequency of the emitter antenna, or of a tank circuit connected thereto, in order to follow the frequency variations of the modulated signal.

17. The system of claim 14, wherein the external control device is arranged for receiving a backscattered signal from the control unit.

18. The implantable device of claim 4 wherein said reduction unit is able to be lubricated by body fluids.

19. Implantable device comprising a driving unit and a kinematic assembly joined together: the driving unit comprising an electric motor driving a first magnetic rotor: the kinematic assembly comprising a second magnetic rotor, magnetically coupled to said first magnetic rotor such that it can be rotationally driven by the motor, and an actuator driven by the second rotor, characterized by an hermetic capsule that encloses the driving unit, the electric motor, and the first rotor; and in that the second magnetic rotor is outside the hermetic capsule, the capsule further includes a control unit arranged for starting and/or stopping and/or reversing the motion of the electric motor, wherein the control unit is arranged for wirelessly exchanging data and/or energy with an external device comprising one or several receiving coils, wherein the control unit is arranged to convert an AC signal picked up by the one or several receiving coils and charge an energy storage means comprised in the hermetic capsule.

20. Implantable device comprising a driving unit and a kinematic assembly joined together: the driving unit comprising an electric motor driving a first magnetic rotor; the kinematic assembly comprising a second magnetic rotor, magnetically coupled to said first magnetic rotor such that it can be rotationally driven by the motor, and an actuator driven by the second rotor, characterized by an hermetic capsule that encloses the driving unit, the electric motor, and the first rotor; and in that the second magnetic rotor is outside the hermetic capsule, the capsule further includes a control unit arranged for starting and/or stopping and/or reversing the motion of the electric motor, wherein the control unit is arranged for wirelessly exchanging data and/or energy with an external device, wherein the control unit is arranged for demodulating a signal transmitted by said external device, the signal comprising a message that is encoded as temporal rates of change of frequency and/or amplitude.

21. A system comprising an implantable device and an external control device, the implantable device comprising a driving unit and a kinematic assembly joined together: the driving unit comprising an electric motor driving a first magnetic rotor; the kinematic assembly comprising a second magnetic rotor, magnetically coupled to said first magnetic rotor such that it can be rotationally driven by the motor, and an actuator driven by the second rotor, characterized by an hermetic capsule that encloses the driving unit, the electric motor, and the first rotor; and in that the second magnetic rotor is outside the hermetic capsule, the capsule further includes a control unit arranged for starting and/or stopping and/or reversing the motion of the electric motor, wherein the control unit is arranged for wirelessly exchanging data and/or energy with the external control device having a transmitting coil arranged to generate and maintain a resonant magnetic field for charging an energy storage means comprised in the hermetic capsule.

22. The system of claim 21, wherein the external control device is arranged for transmitting a signal to said control unit the signal comprising a message that is encoded as temporal rates of change frequency and/or of amplitude.

23. The system of claim 21, comprising a control means arranged to tune automatically the resonance frequency of the emitter antenna, or of a tank circuit connected thereto, in order to follow the frequency variations of the modulated signal.

24. The system of claim 21, wherein the external control device is arranged for receiving a backscattered signal from the control unit.

* * * * *